United States Patent
Lin et al.

(10) Patent No.: US 11,475,994 B2
(45) Date of Patent: Oct. 18, 2022

(54) SYSTEM AND METHOD FOR INFUSION PUMP FOR USE IN AN MR ENVIRONMENT WITH LIGHTING OF USER INTERFACE KEYS TO GIVE CLINICIAN GUIDANCE

(71) Applicant: KONINKLIJKE PHILIPS N.V., Eindhoven (NL)

(72) Inventors: Mark Shih-Chieh Lin, Winter Park, FL (US); Donald Alan Forrer, Jr., Orlando, FL (US); Ronald Paul Consiglio, Clermont, FL (US); John Thomas Judy, Marblehead, MA (US); Francis Patrick O'Neill, Kissimmee, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 45 days.

(21) Appl. No.: 16/333,275

(22) PCT Filed: Sep. 29, 2017

(86) PCT No.: PCT/EP2017/074912
§ 371 (c)(1),
(2) Date: Mar. 14, 2019

(87) PCT Pub. No.: WO2018/060503
PCT Pub. Date: Apr. 5, 2018

(65) Prior Publication Data
US 2019/0252070 A1    Aug. 15, 2019

Related U.S. Application Data

(60) Provisional application No. 62/401,379, filed on Sep. 29, 2016.

(51) Int. Cl.
*G16H 40/63* (2018.01)
*G16H 20/17* (2018.01)

(52) U.S. Cl.
CPC .......... *G16H 40/63* (2018.01); *G16H 20/17* (2018.01)

(58) Field of Classification Search
CPC ........ G16H 20/40; G16H 40/20; G16H 40/63; G16H 40/67; G16H 20/17
(Continued)

(56) References Cited

U.S. PATENT DOCUMENTS

| 5,579,767 A | 12/1996 | Prince |
| 5,637,093 A | 6/1997 | Hyman |

(Continued)

FOREIGN PATENT DOCUMENTS

| EP | 1523021 | 4/2005 | |
| WO | 2015/175183 | 11/2015 | |
| WO | WO-2015175183 A1 * | 11/2015 | ........... G06F 1/1662 |

OTHER PUBLICATIONS

Wilson Hurd; How Backlighting Works in Keyboards—Nelson-Miller, Inc.; https://www.nelson-miller.com/how-backlighting-works-in-keyboards/, 2018 (Year: 2018).*

*Primary Examiner* — Hiep V Nguyen

(57) ABSTRACT

A medical device (10) for use in a Magnetic Resonance environment includes a keypad (22) having keys (24). Light sources (26) are disposed with respective keys of the keypad to illuminate the respective keys. At least one electronic processor (18) is programmed to: perform user interfacing operations in which user inputs are received via the keypad; during the user interfacing operations, control the light sources to selectively illuminate keys usable in the user interfacing operations; and controlling or configuring the medical device in accord with the user inputs received during the user interfacing operations.

10 Claims, 3 Drawing Sheets

(58) Field of Classification Search
USPC .............................................................. 705/2
See application file for complete search history.

(56) References Cited

U.S. PATENT DOCUMENTS

| | | |
|---|---|---|
| 2003/0060765 A1 | 3/2003 | Campbell |
| 2003/0135087 A1 | 7/2003 | Hickle |
| 2005/0073446 A1* | 4/2005 | Lazaridis .............. G06F 3/0202 |
| | | 341/22 |
| 2006/0079758 A1* | 4/2006 | Susi ...................... A61M 5/172 |
| | | 600/420 |
| 2006/0245808 A1 | 11/2006 | Salman |
| 2007/0285913 A1* | 12/2007 | Cybart .............. H04M 1/72466 |
| | | 362/23.15 |
| 2009/0076461 A1 | 3/2009 | Hefele |
| 2009/0091478 A1* | 4/2009 | Chan ........................ G05G 1/02 |
| | | 341/22 |
| 2011/0193704 A1* | 8/2011 | Harper ................... G16H 20/17 |
| | | 340/573.1 |
| 2013/0049628 A1* | 2/2013 | Kwong ................. H05B 45/37 |
| | | 315/250 |
| 2013/0329396 A1* | 12/2013 | Smith .................... G06F 1/1656 |
| | | 362/23.03 |
| 2015/0014249 A1 | 1/2015 | Alberti |

* cited by examiner

SYSTEM AND METHOD FOR INFUSION PUMP FOR USE IN AN MR ENVIRONMENT WITH LIGHTING OF USER INTERFACE KEYS TO GIVE CLINICIAN GUIDANCE

CROSS REFERENCE TO RELATED APPLICATIONS

This application is the U.S. National Phase application under 35 U.S.C. § 371 of International Application No. PCT/EP2017/074912 filed Sep. 29, 2017, published as WO 2018/060503 on Apr. 5, 2018, which claims the benefit of U.S. Provisional Patent Application No. 62/401,379 filed Sep. 29, 2016. These applications are hereby incorporated by reference herein.

FIELD

The following relates generally to the radiology arts, medical infusion arts, infusion pump arts, and related arts.

BACKGROUND

Infusion pumps for general use in the hospital typically are not designed to be safely be used in the Magnetic Resonance Imaging (MRI) environment as they pose serious safety risks to clinicians and patients. Such infusion pumps typically include magnetic materials (e.g. motor components) and generate radio frequency (RF) emissions that can interfere with the MR imaging. MR-compatible infusion pumps have been developed specifically for use in the Magnetic Resonance (MR) examination room environment. In a typical workflow, medical personnel transport the patient on a gurney to the MRI examination facility with the patient connected to a general-purpose infusion pump. At the facility, the patient is switched over to the MR-compatible infusion pump before being moved into the RF-shielded MR room. However, these MR-compatible infusion pumps are different to those the clinician is familiar with, which can lead to setup errors such as incorrect flow rate or other incorrect settings when the MR-compatible infusion pump is connected with the patient.

More generally, difficulties can arise whenever medical personnel are required to operate a medical device with which they lack intimate familiarity.

Improvements disclosed herein address the foregoing and other disadvantages of existing infusion pump systems, methods, and the like.

BRIEF SUMMARY

In accordance with one illustrative example, a medical device for use in a Magnetic Resonance environment includes a keypad having keys. Light sources are disposed with respective keys of the keypad to illuminate the respective keys. At least one electronic processor is programmed to: perform user interfacing operations in which user inputs are received via the keypad; during the user interfacing operations, control the light sources to selectively illuminate keys usable in the user interfacing operations; and controlling or configuring the medical device in accord with the user inputs received during the user interfacing operations.

In accordance with another illustrative example, a method of illuminating a medical device for use in a Magnetic Resonance environment is provided. The method includes: with at least one processor, executing a user-interfacing operation; with the at least one processor, retrieving, from a data storage, data related to indexing the usable keys for the user interfacing operation to control the light sources to selectively illuminate usable keys on a keypad of the medical device; with the at least one processor, selectively illuminating the indexed keys; with at least one key of a keypad of a medical device, receiving at least one user input by the user pressing at least one illuminated key; and with the at least one processor, controlling or configuring the medical device in accord with the received user inputs received by at least one of the illuminated keys; with at least one key of a keypad of a medical device.

In accordance with another illustrative example, a medical pump for use in a Magnetic Resonance environment includes a non-magnetic motorized fluid pump, a keypad having keys, and light emitting diodes (LEDs). An individual LED is disposed behind a corresponding individual key of the keypad to illuminate the respective key. A display is configured to display details of medication-delivery operations of the medical pump corresponding to the illuminated combination of keys. At least one electronic processor is programmed to: perform user interfacing operations in which user inputs are received via the keypad; during the user interfacing operations, control the light sources to selectively illuminate keys usable in the user interfacing operations; and controlling or configuring the medical pump in accord with the user inputs received during the user interfacing operations.

One advantage resides in reducing MR interference generated by a medical device in an MR environment.

Another advantage resides in allowing users of the medical device to make faster decisions regarding operation of the medical device.

Another advantage resides in reducing the chances of error by a user of the medical device.

Another advantage resides in providing a medical device having a keypad that provides visual guidance as to its use in performing specific user interfacing operations.

Further advantages of the present disclosure will be appreciated to those of ordinary skill in the art upon reading and understand the following detailed description. It will be appreciated that a given embodiment may provide none, one, two, or more of these advantages.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the invention.

DETAILED DESCRIPTION

Figure 1:
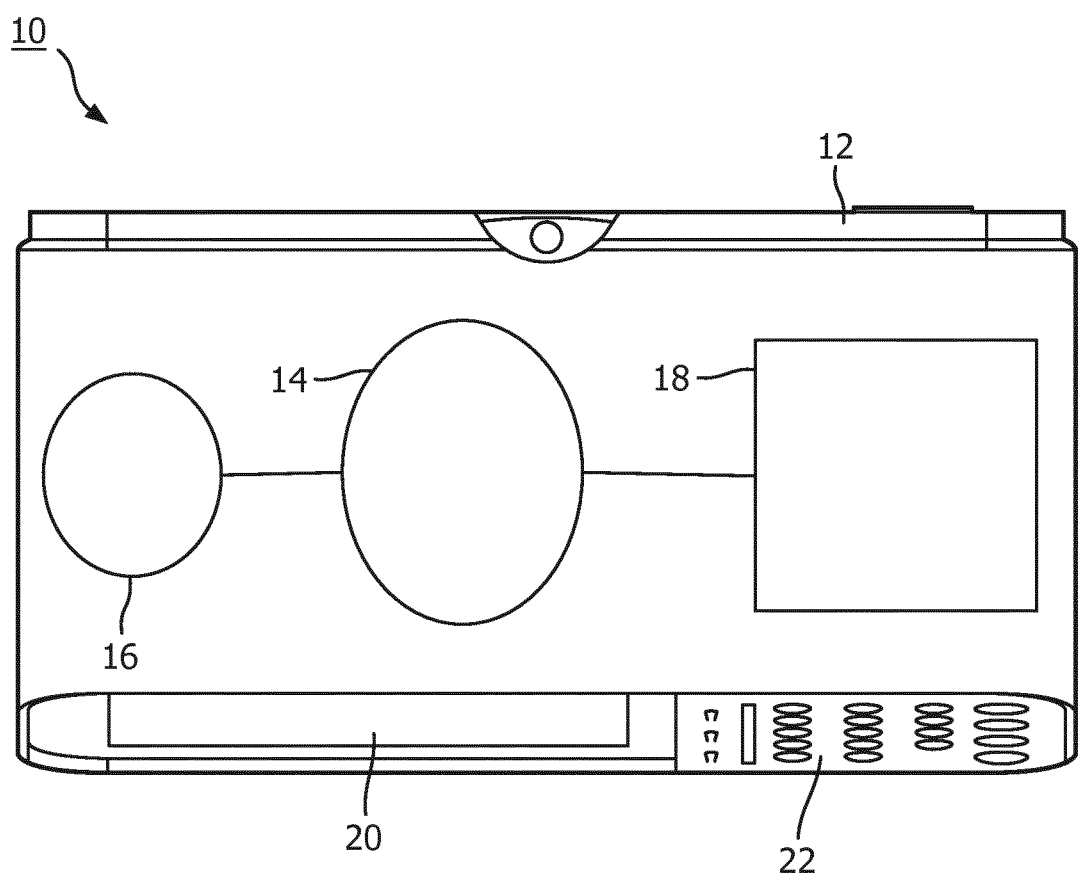
FIG. 1 diagrammatically illustrates a top view of medical device in accordance with one aspect.

Medical devices are increasingly computerized devices, and typically have a generic keypad serving as the user interface device for performing various different user interfacing operations. The use of a single keypad for performing these various operations is generally assumed to simplify operation and thereby benefit the user. However, it is recognized herein that the potential for medically significant errors can actually be increased by the use of such a generic keypad. The keypad-controlled device may have higher complexity due to availability of additional computer-enabled features, and it becomes easier for the user to become confused and believe he or she is responding to one user interfacing operation when in fact is responding to a different user interfacing operation.

For example, in the past, flow rate of an infusion pump might be set by adjusting a flow controller knob, while alarm limits might be set by adjusting knobs associated with the individual alarm devices. In a modern infusion pump, these user interfacing operations are all performed via the single generic keypad. Consequently, it becomes easier for a user to (for example) inadvertently enter the upper flow alarm limit value when actually responding to the flow rate input user interfacing operation, thereby setting the flow rate to a high value that may be medically detrimental for the patient.

The use of electronics in medical devices such as infusion pumps also increases the potential for generating radio frequency (RF) emission that may constitute radio frequency interference (RFI) for a magnetic resonance (MR) imaging device. Thus, these electronic medical devices are problematic for use inside the RF-shielded MR examination room.

In some illustrative embodiments disclosed herein, improved user interfacing via a keypad is provided by way of an illuminated keypad, in which the keys are not continuously illuminated—rather, keys are illuminated only when they are appropriate for use in responding to a data input request. For example, during a pump startup process the display may show a question "enter flow rate", and then only the numeric keys "0"-"9" are illuminated Likewise, if a yes/no query is posed then only the "Y" and "N" keys may be illuminated, and so forth. In this way, the user is guided as to which inputs are acceptable when running through the startup program, and the likelihood of user input error is decreased.

The MR setting or other RFI-sensitive medical settings pose particular difficulties for such contextual keypad lighting. In a medical device for use in an MR room, the device usually employs a non-magnetic motor (if motorized) and has all electronics disposed inside a radio frequency interference (RFI) shield in order to avoid generating MR interference. However, the light produced by an LED indicator light must be visible. The usual solution is to place the LEDs inside the RFI shield and run optical fibers out of the RFI shield to illuminate the keypad—but this solution is problematic for the contextual illumination of the invention since the illumination of each key must be selectively turned on/off (for example, the "8" key may be illuminated if the input calls for a general numeric value, but may be not illuminated if the input calls for a selection of one of four options by pressing a corresponding one of the keys "1", "2", "3", or "4"). To implement such user interfacing operation-specific individual key lighting using optical fibers in this instance, two fibers would need to be run to the "8" key—one from the LED that lights up when a numeric value is to be entered, and a different LED that lights up when a number in the range "1"-"4" is to be selected.

To address this problem, in some embodiments disclosed herein an LED is located behind (or more generally, with) each key of the keypad. To reduce RFI, the LEDs are not driven by pulse width modulation (PWM) or other AC signal, but rather are driven by an analog DC current. Additionally, low-pass filtering can be used to remove any higher frequency harmonics that might otherwise interfere with the MR. It is also contemplated to further reduce RFI by turning the LED on or off using a DC current ramp, so as to reduce high frequency components that are associated with a more abrupt step change in DC current level. For example, a current ramp over a hundred milliseconds or a few hundred milliseconds may not visually perturb the user, but can result in reduced high frequency content making up the D.C. current transition. These measures, individual or in various combinations, reduce the potential for RFI problems. To implement the contextual key illumination, each LED can be powered, or not, in accord with software instructions, e.g. each displayed user interfacing (UI) dialog can have an associated data structure storing the indices of the keys to be illuminated for that UI dialog. When the user interfacing operation is executed by the medical device controller, it reads the associated data structure and powers the LEDs indexed in the data structure. In this approach, a medical device firmware update that changes the keys useable for a particular user interfacing operation merely includes an updated associated data structure.

With reference now to FIG. 1, a schematic illustration of a medical device 10 is shown. In the illustrative example, the medical device 10 is a medical infusion pump, such as a syringe infusion pump or a volumetric infusion pump. The infusion pump 10 includes features that are typically included with conventional infusion pumps. For example, the infusion pump 10 includes a housing 12 that encloses a motorized fluid pump 14, a power source 16 (or power converter, e.g. for converting 120V a.c. building power), and at least one electronic processor 18, for example a microprocessor or microcontroller and associated components such as memory chips. As illustrated in FIG. 1, the infusion pump 10 is shown in top view, and a "top" portion of the housing 12 is removed, so that the (diagrammatically shown) internal components 14, 16, 18 disposed therein are visible. The motorized pump 14 is configured to pump medication or other therapeutic fluid into a patient via suitable tubing (not shown). The motorized fluid pump 14 is diagrammatically indicated in FIG. 1, and will be appreciated to typically include conventional components not shown such as a motor, pump fluid chamber with electronically controlled inlet and/or outlet valves, sensors such as flow meters, and so forth, The motorized fluid pump 14 is powered by the power source 16 (e.g., a battery). The at least one processor 18 is programmed to control operations of the infusion pump 10, as described in more detail below.

Figure 2:
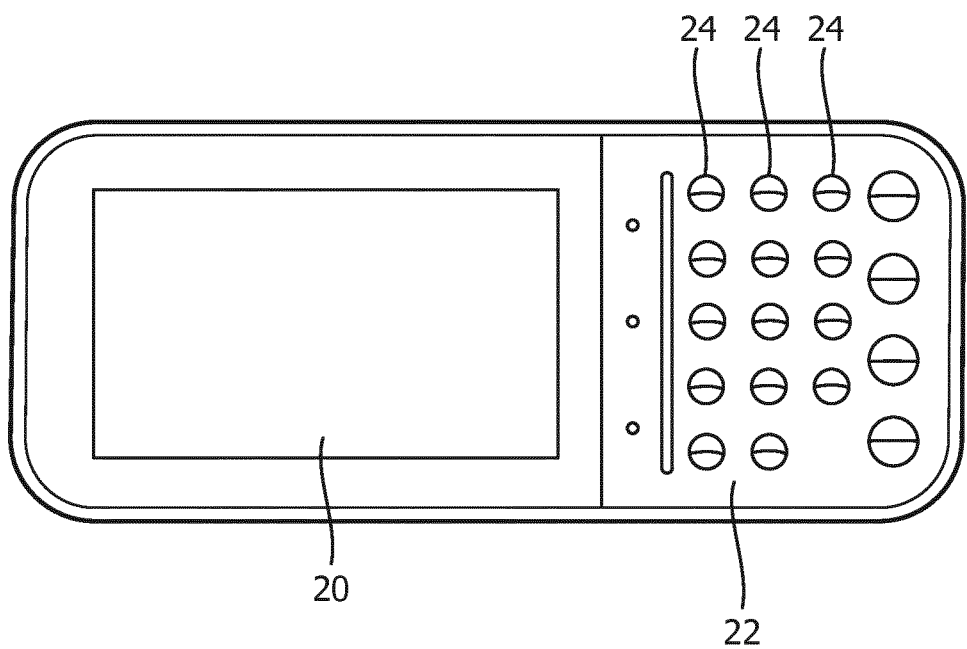
FIG. 2 diagrammatically illustrates a front view of medical device of FIG. 1.

Referring now to FIG. 2 which shows a front view of the infusion pump 10, and with continuing reference to FIG. 1, the infusion pump 10 also includes a display 20 (e.g. an LCD display, cathode ray tube display, seven-segment display, or the like) configured to display details of operations of the infusion pump 10. A keypad 22 is disposed adjacent the display 20. The keypad 22 includes a plurality of keys 24. The keys 24 can be provided for entry of alpha-numeric characters, or commands such as "on," "off," "start," stop", and the like. The keys 24 may be of any type capable of detecting a finger press, e.g. membrane keys, mechanical keys, touch-sensitive capacitive keys, or so forth. The keys 24 are configured to be pressed by a user (e.g., a doctor, a nurse, and the like) to input information during user interfacing operations, e.g. to control medication-delivery operations of the infusion pump 10 (e.g., "on/off," "start delivery," "stop delivery," "increase/decrease rate of delivery," "timer," "and the like). The user interfacing operation may also employ the display 20 to display information pertaining to the operation. Further, as disclosed herein the keys 24 are configured to be illuminated during execution of a user interfacing operation only when they are usable to input information for responding to that user interfacing operation. For example, during power-up of the infusion pump 10, the display 20 may show a question "enter flow rate", and then only the numeric keys "0"-"9" are illuminated. Likewise, if a yes/no query is posed then only the "Y" and "N" keys may be illuminated, and so forth. In this way, the user is guided as to which inputs are acceptable when running through the startup program of the infusion pump 10.

Figure 3:
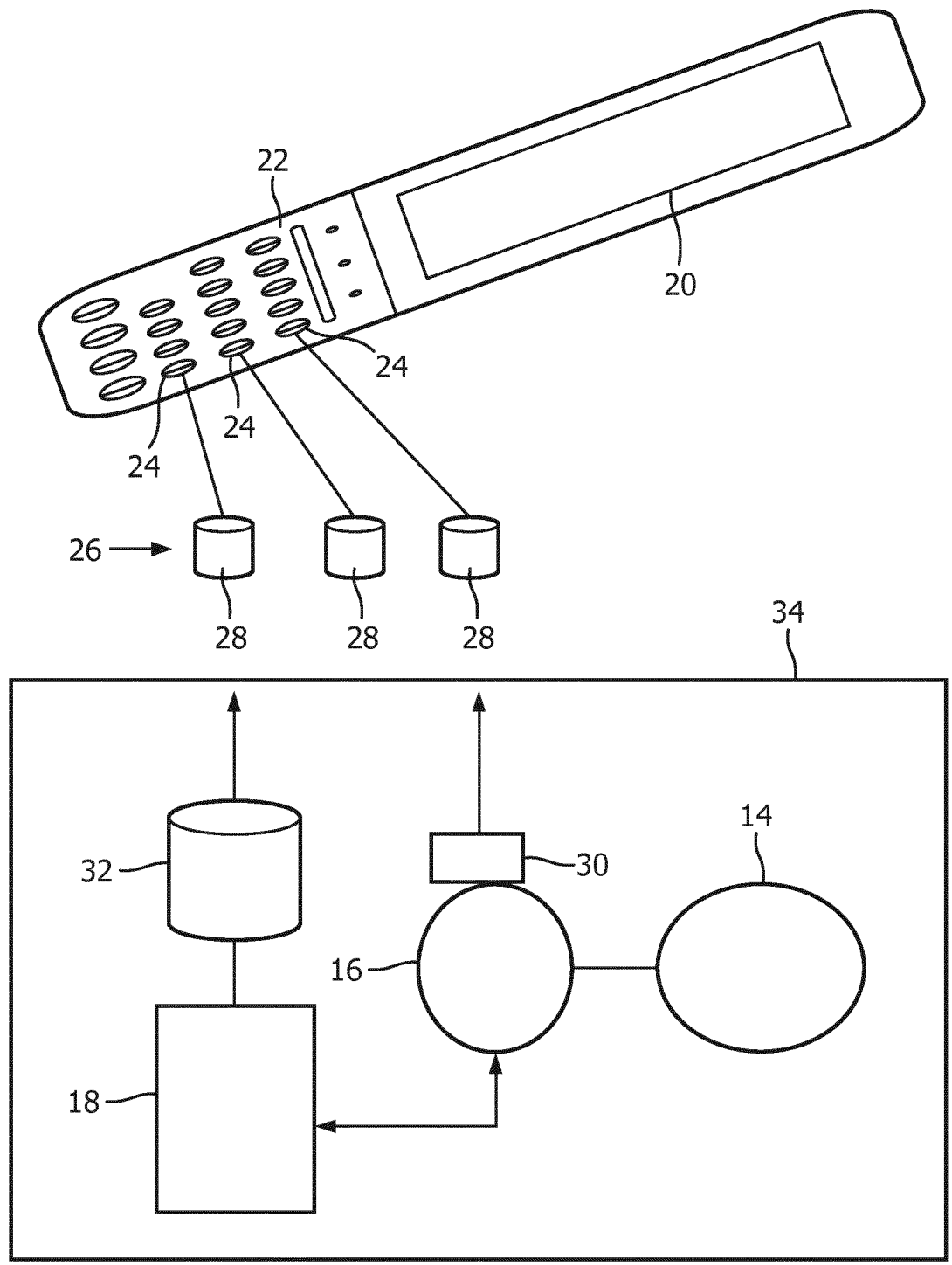
FIG. 3 diagrammatically illustrates electronic components of medical device of FIG. 1.

FIG. 3 shows the keypad 22 in more detail, along with associated electronics. A plurality of light sources 26 is disposed with respective keys 24 of the keypad 22 to illuminate the respective keys. In one example, the light sources 26 can be disposed behind or under the keys 24. In another example, the light sources 26 can be installed within an opening (not shown) in the keys 24. In a further example, the light sources 26 can be installed within or inside of the keys 24, e.g. the key may be a molded component that encapsulates (i.e. overmolds) the light source.

In some embodiments, the plurality of light sources 26 comprises light emitting diodes (LEDs) 28. For example, an individual LED 28 can be disposed behind or underneath a corresponding individual key 24 of the keypad 22. The at least one processor 18 is programmed to control the user-interfacing operations of the infusion pump 10. As used herein, the term "user interfacing operation" entails an operation in which a user enters requested information via the keypad 22. The request for information may be conveyed to the user via the display 20 and/or by another mechanism, such as a speech synthesizer. A given user interfacing operation seeks to acquire particular information, e.g. a flow rate value, an alarm limit value, a choice of device operating mode, or so forth. Typically, only some of the keys 24 are usable in the user interfacing operation. For example, if the user interfacing operation seeks entry of a numeric value, then the usable keys are the keys "0"-"9" and possibly "." (if decimal values are allowable). On the other hand, if the user interfacing operation seeks a "yes" or "no" response then the usable keys may be the "Y" and "N" keys of an alphanumeric keypad, or the usable keys may be special keys labelled "Yes" and "No". As disclosed herein, the light sources 26 are used to illuminate only the usable keys for each user interfacing operation. To do so, the at least one processor 18 is programmed to control the light sources 26 to selectively illuminate keys 24 that are usable in the user-interfacing operations. Once the user input is receive by user operation of the illuminated keys, the at least one processor 18 is programmed to control or configure the infusion pump 10 in accord with the user inputs received during the user interfacing operation(s).

For example, when the user presses one of the keys 24 to turn on the infusion pump 10 (i.e., an on/off key), several of the keys 24 can be illuminated (e.g., "on/off," "start delivery," "increase/decrease rate of delivery," "timer," and the like) to form an illuminated combination of keys. The user can then depress one or more of the keys 24 (e.g., "start delivery," "increase/decrease rate of delivery," "timer," "set delivery rate," and the like) to control the medication-delivery options of the infusion pumps. These medication-delivery operations corresponding to the illuminated combination of keys 24 can be displayed on the display 20. It will be appreciated that the illuminated combination of keys 24 only includes keys corresponding to operations that are available to the user. For example, once the infusion pump 10 is turned on, the "on" key 24 will not be illuminated. Likewise, when the infusion pump 10 is off, only the "on" key 24 will be illuminated. In another example, when the "start delivery" key 24 is pressed, it will no longer be illuminated, leaving only the "off," "stop delivery," "increase/decrease rate of delivery," and "timer" keys 24 (among other possible keys) will remain illuminated. Advantageously, this selective illumination allows the user to make quicker decisions regarding delivery of the medication to the patient, while reducing the number of potential errors the user can make (e.g., by pressing the wrong key 24).

In other embodiments, the at least one processor 18 is configured to operate the power source 16 to deliver power to the LEDs 28. For example, in one embodiment the power source 16 is configured to deliver an analog DC current to the LEDs 28 to operate the LEDs to selectively illuminate the keys 24 usable in the user interfacing operation. (It should be noted that while a single power source 16 is illustrated, there may be a separate power source in the form of a dedicated LED D.C. driver circuit). While using D.C. power substantially reduces RFI emissions of the illuminated keypad, some RFI may still be generated due to D.C. power fluctuations, and/or due to high frequency components of transients, e.g. when the D.C. power is turned on or off. To further reduce RFI, the infusion pump 10 optionally can also include a low-pass filter 30 connected to the electrical conduction path between the LED and its power source 16. The low pass filter 30 is configured to filter the analog DC current delivered to the LEDs 28. For example, if the infusion pump 10 is intended to be MR compatible, the cutoff frequency of the low pass filter is preferably lower than the lowest magnetic resonance frequency of the MR imaging device. In an additional or alternative approach, RFI during D.C. power-on or power-off of an LED can be limited by ramping power up or down. This leverages the reduced high frequency content of a ramp versus a step function. The ramp should be fast enough to not adversely impact user interfacing, e.g. a ramp time of a few milliseconds to a few hundred milliseconds is preferable.

In further embodiments, the infusion pump 10 can include a non-transitory storage 32 (e.g. a flash memory or other solid state memory, a magnetic disk, or so forth) that is configured to store identifications of usable keys 24 during operation of the infusion pump 10. For example, each user interfacing operation can have an associated data structure stored in the data storage 32. The data structure for each user interfacing operation contains index values of all keys of the keypad 22 that are usable in that user interfacing operation. For each user interfacing operation to be performed, the at least one processor 18 is programmed to identify the set of keys 24 usable in the user interfacing operation to be performed by reading the non-transitory storage 32 and controls the light sources 26 to selectively illuminate the identified keys.

It will be appreciated that the medical device 10 (i.e., the infusion pump 10) is configured for use in an MR environment to avoid generating MR interference. To do so, the infusion pump 10 includes a radio frequency interference (RFI) shield 34. However, the RF shield 34 does not surround the keypad 22 and the light sources 26, since these are exposed to the user. In addition, the components of the infusion pump 10, in particular the motorized pump 14, are made from non-magnetic materials so as to avoid magnetic interference and prevent the possibility of the magnetic material being attracted and drawn into the MR bore by the very strong magnetic field (e.g. 3 Tesla in some commercial MRI devices).

Figure 4:
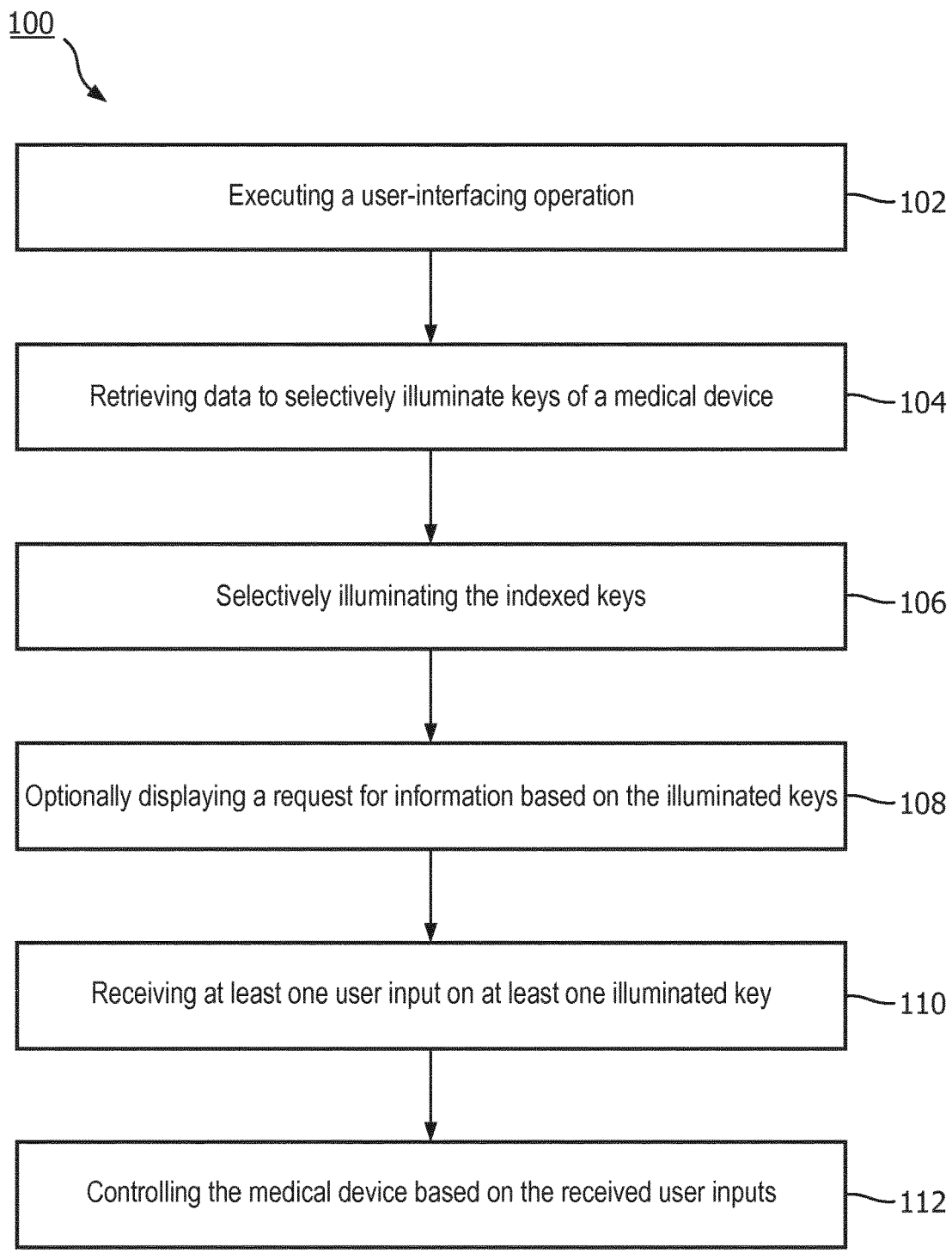
FIG. 4 diagrammatically illustrates a medical device illumination method suitably performed using the medical device of FIG. 1.

With reference now to FIG. 4, a medical device illumination method 100 for use in an MR environment is shown.

At step 102, a user-interfacing operation is executed with the at least one electronic processor 18. At step 104, to control the light sources 26, 28 to selectively illuminate usable keys 24 on the keypad 22 of the medical device 10, data related to indexing the usable keys for the user interfacing operation is retrieved from the data storage 32. At step 106, the LEDs 28 associated with those indexed keys 24 are selectively illuminated to inform the user that these are the usable keys. At step 108 (which may not apply for some user interfacing operations), an information request is displayed on the display 20, such as a request for information, e.g. "Flow rate (ml/sec). At step 110, at least one user input is received by the user pressing at least one illuminated key 24. At step 112, with the at least one processor 18, the medical device 10 is controlled or configured in accord with the received user inputs received by at least one of the illuminated keys 24. This method 100 may be repeated to perform various user interfacing operations Some user interfacing operations may not use the display 20. For example, while delivering IV fluid to the patient, a "flow interruption" user interfacing operation may be executing. This operation may, for example, allow the user to select the "STOP" key to stop IV flow, or to select to adjust the flow rate up or down by pressing up or down arrow key, respectively For this user interfacing operation, the retrieved data structure will index the "STOP", "UP ARROW", and "DOWN ARROW" keys and these will then be illuminated—but the display 20 will continue to display the measured flow or other relevant information.

It will be appreciated that the illustrative data processing or data interfacing components of the medical device 10 may be embodied as a non-transitory storage medium storing instructions executable by an electronic processor (e.g. the at least one electronic processor 18) to perform the disclosed operations. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical device for use in a Magnetic Resonance environment, the medical device comprising:
    a keypad having a plurality of individual keys;
    a plurality of individual light emitting diodes (LEDs), wherein a single one of the individual LEDs is disposed behind a corresponding one of the plurality of individual keys of the keypad to illuminate each respective one of the plurality of individual keys;
    a power source to deliver analog DC current to the plurality of individual LEDs; and
    at least one electronic processor programmed to:
    perform user interfacing operations in which user inputs are received via the keypad;
    during the user interfacing operations, control the LEDs to selectively illuminate keys usable in the user interfacing operations by operating the power source thereby turning on and off the LEDs using a DC current ramp; and
    control or configure the medical device in accord with the user inputs received during the user interfacing operations.

2. The medical device according to claim 1, further comprising a display configured to display details of medication-delivery operations of the medical device corresponding to an illuminated combination of keys.

3. The medical device according to claim 2, further comprising:
    a non-transitory storage storing, for each user interfacing operation, identification of a set of keys usable in the user interfacing operation, wherein, for each user interfacing operation to be performed, the at least one electronic processor is programmed to identify the set of keys usable in the user interfacing operation to be performed by reading the non-transitory storage and controls the each of the plurality of individual LEDs to selectively illuminate the identified keys.

4. The medical device according to claim 1, further comprising:
    a low-pass filter connected to filter the analog DC current delivered to the plurality of individual LEDs.

5. The medical device according claim 1, further comprising a radio frequency interference shield surrounding at least a portion of the keypad and the each of the plurality of individual LEDs.

6. A medical pump, comprising
    a non-magnetic motorized fluid pump; and
    a medical device, a keypad having a plurality of individual keys;
    a plurality of individual light emitting diodes (LEDs) light sources, wherein a single one of the plurality of individual LEDs is disposed behind a corresponding one of the plurality of individual keys of the keypad to illuminate each respective one of the plurality of individual keys;
    a power source to deliver analog DC current to the plurality of individual LEDs; and
    at least one electronic processor programmed to:
    perform user interfacing operations in which user inputs are received via the keypad;
    during the user interfacing operations, control the :LEDs to selectively illuminate keys usable in the user interfacing operations by operating the power source thereby turning on and oft the LEDs using a DC current ramp; and
    control or configure the medical device in accord with the user inputs received during the user interfacing operations.

7. The medical pump according to claim 6, wherein the medical device further comprises a display configured to display details of medication-delivery operations of the medical device corresponding to an illuminated combination of keys.

8. A method of illuminating a medical device for use in a Magnetic Resonance environment, the medical device comprising a keypad having keys and light sources comprising light emitting diodes (LEDs), an individual LED being disposed behind a corresponding individual key, the method comprising:
    with at least one processor, executing a user-interfacing operation;
    with at least one processor, retrieving, from a data storage, data related to indexing a plurality of usable keys for the user interfacing operation to control a plurality of individual LEDs to selectively illuminate usable keys on a keypad of the medical device, wherein a single one of the individual LEDs is disposed behind a corresponding one of the plurality of usable keys;

with the at least one processor, selectively illuminating selected ones of the plurality of usable keys by delivering, with a power source, analog DC current to the LEDs to operate the LEDs to selectively illuminate the usable keys in the user interfacing operations, and turning on and off the LEDs using a DC current ramp;

with at least one key of the keypad of the medical device, receiving at least one user input by the user pressing at least one illuminated key; and with the at least one processor, controlling or configuring the medical device in accord with the received user inputs received by at least one of the illuminated keys.

9. The method according to claim 8, further comprising:

filtering, with a low-pass filter the analog DC current delivered to the plurality of individual LEDs.

10. The method according to claim 8, further comprising:

storing, with a non-transitory storage identification of a set of the plurality of useable keys, for each user interfacing operation, usable in the user interfacing operation; and with the at least one processor, for each user interfacing operation to be performed, identifying the plurality of useable keys in the user interfacing operation to be performed by reading the non-transitory storage and controls the plurality of individual LEDs to selectively illuminate the identified plurality of useable keys.

* * * * *